United States Patent [19]

Masuda

[11] Patent Number: 4,808,417

[45] Date of Patent: Feb. 28, 1989

[54] FEED ADDITIVE FOR FISH CULTIVATION

[75] Inventor: Takashi Masuda, Tokyo, Japan

[73] Assignee: Toa Pharmaceutical Co., Ltd., Tokyo, Japan

[21] Appl. No.: 130,283

[22] Filed: Dec. 8, 1987

[30] Foreign Application Priority Data

Dec. 27, 1986 [JP] Japan .................................. 61-309105
Dec. 27, 1986 [JP] Japan .................................. 61-309106

[51] Int. Cl.⁴ .............................................. A23K 1/18
[52] U.S. Cl. .......................................... 426/2; 426/53; 426/54; 426/63; 426/62; 426/807; 426/623
[58] Field of Search ...................... 426/656, 7, 807, 1, 426/61, 62, 63, 2, 623, 53-54

[56] References Cited

U.S. PATENT DOCUMENTS

| | | | |
|---|---|---|---|
| 3,591,389 | 7/1971 | Schneider | 426/805 |
| 4,239,782 | 12/1980 | Cinquemani | 426/805 |

FOREIGN PATENT DOCUMENTS

| | | | |
|---|---|---|---|
| 1692400 | 10/1977 | Fed. Rep. of Germany | 426/805 |
| 3306027 | 8/1984 | Fed. Rep. of Germany | 426/805 |
| 0121441 | 9/1981 | Japan | 426/805 |

*Primary Examiner*—Marianne Cintins
*Attorney, Agent, or Firm*—Toren, McGeady & Associates

[57] ABSTRACT

A feed additive for fish cultivation, which contains, as effective components, a proteinase, lipase, and mixture of three kinds of bacteria consisting of lactic acid producing microbe, saccarificating microbe, and butyric acid producing microbe.

20 Claims, No Drawings

FEED ADDITIVE FOR FISH CULTIVATION

BACKGROUND OF THE INVENTION

Field of the Invention

The present invention relates to a feed additive for fish cultivation and more particularly it relates to an improvement of the productivity of fish cultivation by promoting digestion and absorption of nutrients included in feeds.

The growth of fish depends on the quality and quantity of the feed used, and in fish cultivation, a technique is required whereby a lot of fish are raised most efficiently within a restricted water area. Recently the output of cultivated fish has increased surprisingly, and with the resultant increment in the quantity of feed consumed, studies on assorted feeds have progressed and ways to use a feed more effectively have been investigated.

Protein, which is an essential nutrient for growth of animals and maintenance of life, participates in the composition of each tissue in the animal body, and also plays an important role as a component of enzymes and hormones. Fish, in general, have a high nutritional requirement for protein (2-4 times the requirement for live stock) and, on the other hand, have a low digestive and metabolic ability toward carbohydrate, so that they have high dependency on protein as an energy source. In many cases, therefore, the assorted feed for fish cultivation contains proteins in an amount of about 40-45%, about 2 to 2.5 times more than that for domestic animals.

The assorted feed for fish cultivation is dependent for protein raw material mainly upon animal protein resources, but the capacity of such resources has its limit. Hence, although it is desired to find new protein resources for the long term, to solve the present problem, studies have been required to determine the best means for the effective utilization of protein resources which are used today as a feed.

When fish meal, which has been the principal animal protein raw material in assorted feeds for fish cultivation, is compared with raw food, the former is considered to be inferior to the latter with respect to the rate of growth of fish, although there is little difference in the analysis of the nutritional constituents between the two feeds. The reason for the inferiority of fish meal is that the digestion rate, or the rate at which the feed is digested and absorbed by fish is low. An improvement in the digestion rate, therefore, would signify the more effective utilization of protein resources.

Furthermore, to allow proteins to be used as a substantial growth promoting factor, which is an original function, it is important that lipids present be effectively utilized as an energy source.

Attempts to improve the digestion rate of nutrients by adding a digestive enzyme to the assorted feed for fish cultivation have been made since the 1960s and some effects have been confirmed, but further technical developments are necessary for their practical use.

SUMMARY OF THE INVENTION

During efforts to develop means for adding digestive enzymes effectively to feeds, especially proteinase and lipase, studies of methods to improve the ability of fish to absorb nutrients in the intestinal tract have been carried out which have resulted in the discovery of the additive of the present invention.

The present invention involves a feed additive for fish cultivation, which contains, as effective components, a proteinase, lipase, and a viable microbial mixture consisting of lactic acid producing bacteria (hereinafter will be called LB), saccarificating bacteria (SB), and butyric acid producing bacteria (BB).

Viable bacteria play an important role in various fields of the applied microbiological industry. When different kinds of viable bacteria, in the state of coexistence, are orally administered to human beings or animals, the cooperative action of the bacteria or the favorable effect that coexisting microbes exert on each other is occasionally desired in a living body, especially in the digestive tract, but there are only a few products in which the symbiotic phenomenon is actively utilized.

DETAILED DESCRIPTION OF THE INVENTION

The present inventors have studied the utilization of viable microbial mixtures which show cooperative behavior for some time, and have investigated and prepared mixtures of three kinds of bacteria consisting of LB, SB and BB, and also have succeeded in utilizing such mixture as effective components of a fish feed additive. The mixture of three kinds of bacteria induces a symbiotic phenomenon in the intestinal tract of fishes and then increases useful bacteria. The resultant normal bowel movement due to the modification and maintenance of normal intestinal flora enhances the ability of the intestinal tract to absorb nutritional components.

The facts suggesting that the mixture of three kinds of bacteria shows a tendency to enhance the growth of bacteria in the living body, as a result of cooperative action, are proved by the following experiments.

(1) Cooperative action between SB and LB

When LB grown in a single culture or in the same medium but supplemented with the filtrate of saccarificating microbial culture solution were compared, the count was shown to be about 100 times more in the latter method than that in the former. This cooperative action is considered to be based on the following: proteinase and amylase yielded by SB in the course of cultivation decompose the surrounding proteins and sugars to produce amino acids (e.g. glutamic acid and aspartic acid) and glucose, respectively, which are essential for the nutritional resources of LB, and thus promote the growth of LB.

(2) Cooperative action between LB and BB

In the comparison of a single culture of respective bateria with a mixed culture of both bacteria, the BB counts were observed to be about ten-fold higher in the latter method than in the former, and the latter method also increased LB counts several times over that of the former. A possible explanation of this cooperative action is that respective bacteria produce a growth promoting factor useful for each other during their cultivation.

Proper samples of respective bacteria composing the mixture of three kinds of bacteria will be listed below.

Examples of LB are:
*Streptococcus faecalis, Streptococcus faecium, Streptococcus lactis, Streptococcus thermophilus,*

*Lactobacillus bulgaris, Lactobacillus jugurt, Lactobacillus acidophilus, Lactobacillus plantarum, Lactobacillus bifidus,*

*Bifidobacterium bifidum, Bifidobacterium infantis, Bificobacterium longum;*

Examples of SB are:
*Bacillus mesentericus, Bacillus subtilis, Bacillus natto;*
Examples of BB are:
*Clostridium butyricum, Clostridium acetobutyricum.*

Three kinds of viable bacteria are prepared as the active principle containing $10^6$–$10^{10}$ bacteria/g each and then mixed to obtain a mixture of three kinds of bacteria. The mixing ratio is preferably 1 to 8 parts of SB or BB against 1 part of LB. Incidentally, when SB and BB are used after forming spores, their properties such as heat resistance, dry resistance, and drug resistance are enhanced.

For the embodiment of the present invention, both proteinase and lipase should be selected according to the sort of constituent of an assorted feed to which the present preparation is added.

Examples of proteinase used are bacterial proteinases, which are distinguished by the sort of bacteria, actinomyces proteinases and filamentous fungus proteinases. Especially, filamentous fungus proteinases, yielded by bacteria belonging to the Genus Aspergillus and Genus Rhizopus, have been used frequently. Furthermore, according to optimal pH, an acid proteinase, neutral proteinase, or alkaline proteinase is chosen.

As for a lipase, the enzymes yielded by bacteria belonging to the Genus Rhizopus and Genus Candida are used frequently.

Other than the aforesaid effective components, nutrition supplement materials such as a yeast, gluten meal, wheat flour, rice-bran oil cake, corn starch, potato starch, lactose, soybean cake and glucose are also effective and added at need. Especially, since a yeast serves as a growth promoting factor to viable bacteria, if added to the effective components, it makes it possible to maintain the viabl microbial count constant.

Fish cultivated in accordance with the present invention include the yound yellowtail (*Seriola quinqueradiata*), porgy, salmon, eel, rainbow trout, carp and ayu. During cultivation, the additive of the present invention is combined with the raw food, moist pellet and assorted feeds. Ordinarily, the feed according to the present invention is added at a ratio of 0.1 to 2.5%, the ratio being adjusted depending on the conditions, for example, the variety of fish, age, type of feed and environment in the water area of cultivation, such as water temperatures and the number of fish cultured.

In fish cultured with the feed supplemented with the feed additive according to the present invention, beneficial intestinal bacteria increase due to the cooperative action of three kinds of bacteria, a normal bowel movement results, due to the modification, and improved maintenance of intestinal flora and digestive action occurs as a result of digestive enzymes which work synergistically to promote the digestion and absorption of nutrients, all of which serve to improve the fish under cultivation.

The beneficial results of ingestion of food supplemented with the additive of the invention include: elongation of the body, increment of fish ratio, quick ingestion of feeds, increase in secretion of slime at the surface of the body, improvement in color of the body, inclusion of proper fat in fish and improvement in taste, decrease in both the morbidity and mortality, reduction of the smell of feces and, coincidently, solidification of feces into a small grain, and resulting reduction of pollution in the water area of fish cultivation due to the easy elimination of feces.

DETAILED DESCRIPTION OF THE PREFERRED EMBODIMENTS

The following examples describe the present invention in detail, but the present invention is not limited to these examples.

Example 1

| Composition of feed additive per 1000 g: | |
|---|---|
| Active principle of LB (Note 1) ($5 \times 10^8$ bacteria/g) | 20 g |
| Active principle of SB (spore) (Note 2) ($5 \times 10^6$/g) | 20 g |
| Active principle of BB (spore) (Note 3) ($5 \times 10^7$/g) | 20 g |
| Proteinase (Note 4) | 100,000 units |
| Lipase (Note 5) | 400,000 units |
| Beer yeast (a nutrition supplement) | proper quantity |
| Natural alminium silicate (a vehicle) | proper quantity |

(Note 1) *Streptococcus faecalis* T-110, Deposition No. 8936, was used; it was deposited with the international deposit agency in Japan, Fermentation Research Institute, Agency of Industrial Science and Technology, Ministry of International Trade and Industry.
(Note 2) *Bacillus mesentericus* TO-A, Deposition No. 8934.
(Note 3) *Clostridium butyricum* TO-A, Deposition No. 8935.
(Note 4) Alkaline proteinase yielded from the bacteria belonging to Genus Rhizopus.
(Note 5) Alkaline lipase yielded from the bacteria belonging to Genus Rhizopus.

(Application Example)

Purpose: To investigate the effect of a feed additive on growth promotion of fishes, field studies were made using rainbow trout.

Test method: An outdoor test pond (made of concrete) was divided along a stream into three parts by a board, and two net crawls (5-mm meshes), 1 m × 1 m × 0.8 m (depth), in each division were settled at intervals of about 0.5 meters. Spring water (14.5°–15.0° C.) was flowed into this pond at the rate of 300 l/min, and the depth of water was controlled at about 0.6 meters.

The rainbow trout of the same venter, at about 7 months after hatching, were divided at random into 6 groups (30 fishes per group) and cultivated preliminarily with the same feed as used in the field studies for two weeks, then field studies were carried out (for 8 weeks in July to September).

According to the feed supply rate table by Leitritz et al., a test feed was given in principle at 2.3% of body weight a day for the average body weight of 23–40 g and 1.9% for 40–60 g. The feed was given twice a day, at 10 and 15 o'clock, for 6 days (not given on Sunday). As a basic feed for the test feed, the assorted feed for cultivating the rainbow trout (Oriental Mark, solid type No. 3), which meets standard requirements, was used.

Three sorts of test feeds, a control feed not containing additives, feeds containing additives in an amount of 0.5% and 2%, were prepared and used for field studies.

Prior to and after the studies, all fish were weighed, the length of the fish was measured, and the corpulence rate was estimated. Total body weight in each group was measured every 2 weeks, and feed efficiency and body-weight increase rate were estimated.

In a comparison control group, the feed not containing the additives (group A), that containing the additives in an amount of 0.5% (group B), and that containing the additives in an amount of 2% (group C) were supplied.

The studies were carried out in duplicate and called A-1, A-2, B-1, B-2, C-1 and C-2. Groups belonging to 1 were located on the upper stream of the pond and groups belonging to 2 on the downstream.

Test Results: As for the feed efficiency (Note 6), the average of control group (A) was 59.4% (A-1: 64.4%, A-2: 54.4%), the average of control group containing 0.5% of additives (B) 67.4% (B-1: 67.5%, B-2: 67.3%), and the average of control group containing 2% (C) 67.1% (C-1: 74.6%, C-2: 59.5%), and when compared with the average value, group B was higher than group A by 8.0%, group C was higher than A by 7.7%, and groups B and C are almost the same (difference 0.3%). Comparisons among the groups located on the upper stream show that: group C was higher than group A by 10.2% and higher than group B by 7.1%, and on the downstream group B was higher than group A by 12.9% and higher than group C by 7.8%. That is to say, the difference in feed efficiency between the control group and addition group, fed food containing additive of the invention; was shown to be 10–13% in both groups located on the upper stream and downstream, and it was clear that the additives do take part in improvement of the feed efficiency.

As for the increase rate of body weight (Note 7), group A was 72.7% on the average (A-1: 79.9%, A-2: 65.4%), group B 84.7% (B-1: 84.9%, B-2: 84.5%), and group C 84.2% (C-1: 94.5%, C-2: 73.8%). The rate of increase in the addition groups was higher than that of the control group by about 12% on the average, showing a similar tendency to the feed efficiency. From these results, it was confirmed that the feed additives for fish cultivation according to the present invention played a part in digestion and absorption of feeds in the cultivation of rainbow trout and had some effects of improving the feed efficiency and increasing the rate of body weight gain.

(Note 6)

$$\text{Feed efficiency} = \frac{G_1 - G_2 + G_3}{G_4} \times 100$$

(Note 7)

$$\text{Increase rate of body weight} = \frac{G_1 - G_2 + G_3}{G_2} \times 100$$

$G_1$: total body weight after the test
$G_2$: total body weight before the test
$G_3$: total body weight in the dead fish
$G_4$: total amount of the feed supplied Test Results (Summary)

|  |  | Control | | Addition (0.5%) | | Addition (2%) | |
| --- | --- | --- | --- | --- | --- | --- | --- |
|  |  | A-1 (Upperstream) | A-2 (Downstream) | B-1 (Upperstream) | B-2 (Downstream) | C-1 (Upperstream) | C-2 (Downstream) |
| Total Number of Fish | 1 Start | 30 | 30 | 30 | 30 | 30 | 30 |
|  | 2 14 days | 30 | 30 | 30 | 30 | 30 | 30 |
|  | 3 28 days | 30 | 30 | 30 | 30 | 30 | 30 |
|  | 4 42 days | 30 | 30 | 30 | 30 | 30 | 30 |
|  | 5 56 days | 30 | 30 | 30 | 30 | 30 | 30 |
| Total Weight (g) | 1 Start | 1052.1 | 1015.7 | 1041.9 | 1054.7 | 1042.6 | 1122.3 |
|  | 2 14 days | 1170 | 1120 | 1180 | 1190 | 1170 | 1250 |
|  | 3 28 days | 1410 | 1310 | 1410 | 1430 | 1420 | 1530 |
|  | 4 42 days | 1620 | 1450 | 1640 | 1660 | 1690 | 1700 |
|  | 5 56 days | 1892.6 | 1679.7 | 1926.2 | 1945.9 | 2027.6 | 1950.4 |
| Average Body Weight (g) | 1 Start | 35.1 | 33.9 | 34.7 | 35.2 | 34.8 | 37.4 |
|  | 2 14 days | 39.0 | 37.3 | 39.3 | 39.7 | 39.0 | 41.7 |
|  | 3 28 days | 47.0 | 43.7 | 47.0 | 47.7 | 47.3 | 51.0 |
|  | 4 42 days | 54.0 | 48.3 | 54.7 | 55.3 | 56.3 | 56.7 |
|  | 5 56 days | 63.1 | 56.0 | 64.2 | 64.9 | 67.6 | 65.0 |
| Number of Dead Fish | I term | 0 | 0 | 0 | 0 | 0 | 0 |
|  | II term | 0 | 0 | 0 | 0 | 0 | 0 |
|  | III term | 0 | 0 | 0 | 0 | 0 | 0 |
|  | IV term | 0 | 0 | 0 | 0 | 0 | 0 |
|  | Mortality | 0 | 0 | 0 | 0 | 0 | 0 |
| Quantity of Feed (g) | I term | 290.4 | 280.8 | 288.0 | 291.6 | 288.0 | 309.6 |
|  | II term | 322.8 | 309.6 | 325.2 | 328.8 | 322.8 | 345.6 |
|  | III term | 321.6 | 298.8 | 321.6 | 326.4 | 324.0 | 349.2 |
|  | IV term | 369.6 | 331.2 | 374.4 | 378.0 | 385.2 | 387.6 |
| Increase Rate of Body Weight (%) | I term | 11.2 | 10.3 | 13.3 | 12.8 | 12.2 | 11.4 |
|  | II term | 20.5 | 17.0 | 19.5 | 20.2 | 21.4 | 22.4 |
|  | III term | 14.9 | 10.7 | 16.3 | 16.1 | 19.0 | 11.1 |
|  | IV term | 16.8 | 15.8 | 17.5 | 17.2 | 20.0 | 14.7 |
| Feed Efficiency (%) | I term | 40.6 | 37.1 | 48.0 | 46.4 | 44.2 | 41.2 |
|  | II term | 74.3 | 61.4 | 70.7 | 73.0 | 77.4 | 81.0 |
|  | III term | 65.3 | 46.9 | 71.5 | 70.5 | 83.3 | 48.7 |
|  | IV term | 73.8 | 69.4 | 76.4 | 75.6 | 87.6 | 64.7 |
| Quantity of Sample per kg of Body Weight (g) | I term | 0 | 0 | 1.38 | 1.38 | 5.52 | 5.52 |
|  | II term | 0 | 0 | 1.38 | 1.38 | 5.52 | 5.53 |
|  | III term | 0 | 0 | 1.14 | 1.14 | 4.56 | 4.56 |
|  | IV term | 0 | 0 | 1.14 | 1.14 | 4.56 | 4.56 |

Example 2

Composition of the feed additive per 1000 g:

| Active principle of LB (Note 1) ($1 \times 10^9$ bacteria/g) | 25 g |
| --- | --- |
| Active principle of SB (spore) (Note 2) | 40 g |

| -continued | |
|---|---|
| (1 × 10⁷/g) | |
| Active principle of BB (spore) (Note 3) | 55 g |
| (1 × 10⁸/g) | |
| Proteinase (Note 4) | 150,000 units |
| Lipase (Note 5) | 300,000 units |
| Dry yeast (a nutrition supplement) | proper quantity |
| Lactose (a nutrition supplement and vehicle) | proper quantity |
| Wheat flour (a nutrition supplement and vehicle) | proper quantity |

(Note 1) *Lactobacillus acidophillus* was used.
(Note 2) *Bacillus subtilis* was used.
(Note 3) *Clostridium acetobutyricum* was used.
(Note 4) A proteinase yielded from the bacteria belonging to Genus Aspergillus, showing a maximum enzymatic activity at about pH 8.0.
(Note 5) A neutral of alkaline lipase yielded from the bacteria belonging to Genus Rhizopus.

In the example, a proteinase showing a maximum enzymatic activity at about pH 8.0 was used, which is a property close to a proteinase in the pyloric cecum and intestine of the fish, especially rainbow trout, and hence it is a suitable one for cultivating the fish.

Examples of Use of Additive of Invention

1. Effect of the additive of the present invention on digestion and absorption in the rainbow trout (test period: May to September)

The rainbow trout, at 6 months after hatching were divided into 3 groups, 30 fishes a group, and tests were made (the average body weight was 166–188 g). Spring water, which temperature was 12° C., was flowed in at a rate of 202 l/min. The quantity of feed supplied was 1% of the body weight a day according to the feed-supply rate table by Leitritz et al. and the feed was given twice, at 9 and 14 hours. In the control group, the feed did not contain the additive. Test feed contained the additive in an amount of 0.5% and 2.0%. As a basic feed, the assorted feed for growing the rainbow trout, which met standard requirements, was employed. To each feed chrome oxide was added by 0.5% as an indicator.

The digestion absorption rate of crude protein was 84.9% in the control group, and 85.0–87.4% in the addition groups, showing that the rate in the addition groups was statistically significant compared with that in the control group. Furthermore, the digestion absorption rate of crude lipid was 78.3% in the control group and 81.6–84.3% in the addition groups, showing statistically significant results in the addition groups.

From these results, it was confirmed that the additive of the present invention brought about improved digestion and absorption of feed.

2. Field studies of the assorted feed supplemented with the additive of the present invention for a young yellowtail (test period: November to February)

In a polyethylene crawl connected to a raft which is divided into small sections at the surface of sea, the young yellowtail of 50 fishes each, having an average body weight of 709 g, were grown, and tests were carried out. Feed used for tests were (A) raw food (sardines), (B) assorted feed: the combination of compound, water, and squid oil; and the combination of compound, raw food (any one of the mackerel, sand eel, and sardine), and squid oil, (C) the feed plus the additive of the present invention: the combination of compound, raw food (sardines), squid oil, and the additive (1.5%). (B) and (C) were given in the form of moist pellet. At the beginning, middle, and end of the test, all fish in each group were weighed, and the state of the remnant of feed was observed every day. In the last day of the test, a sensuous test was carried out by 12 persons concerning the color of fish, hardness in the muscle, the degree of fat, and taste.

The state of ingestion was observed to be extremely good in both the additive group (C) and raw food group (A), but bad in the assorted feed group (B). Increase in the body weight was observed in the raw food group (A), the additive group (C), and the assorted feed plus mackerel group (B-mackerel); feed efficiency estimated in dried substance were 32%, 18%, and 14%, respectively. Dead fish throughout the test period was 1 in the raw food group (A), 5 in the additive group (C), 12 in the assorted feed plus mackerel group (B-mackerel), and 22 to 27 in the assorted feed plus others group (B-others). In the sensuous test, the sum of "delicious" and "a little delicious" taste was 67% in the additive group (C) and was in the order of the assorted feed plus sardine group (B-sardine; 60%) and the raw food group (A; 54%), winning the reputation of the feed plus raw food, sardine, group.

Furthermore, the digestion-absorption rate of protein was determined in the contents of the intestine of a young yellowtail cultivated with the combined feed of compound, raw food (a sardine), and squid oil and with those plus 1% of additive, and results were 76.3% in the additive group and 69.1% in the control group, showing a rise of 7% of the digestion-absorption rate by the addition of additive. In these tests, some improvements were observed on the ingestion, growth of fish, and mortality. They are considered to be the result of the improvement of the texture of the feeds and the digestion absorption rate of feeds by addition of the additive of the present invention.

3. Preventive effect of the additive on the pollution of cultivating water by fish feces (test period: October to November)

In group (A) the rainbow trout, at 9 months after hatching, were divided into 3 groups, 150 fish per group, and tests were made (the average body weight was about 100 g). Spring water, having a temperature of 12° C., was flowed at a rate of 202 l/min. The quantity of the feed supplied was 1.1% of the body weight a day on the basis of the table of feed supply rate by Leitritz et al., and the feed was given twice, 10 and 15 hours. In group (B) the rainbow trout, at 7 months after hatching, were divided into 3 groups, 960 fish per group, and tests were made (the average body weight was 20.8 g). Spring water, 11.5° C., was flowed at a rate of 202 l/min. The quantity of feed supplied was 2.1% of the body weight a day on the basis of the table of feed supply rate by Leitritz et al., and the feed was given twice, 10 and 15 o'clock.

As a control feed, the feed not containing the additive was used. As a test feed, feeds containing the additive in an amount of 0.5% and 2.0% were prepared. As the basic food in each feed, the assorted feed for cultivating rainbow trout, which meets standard requirements, was employed. Chrome oxide was added to each feed in an amount of 0.5% as an indicator.

The feces were diluted with a diluent (spring water exposed to air in the pond) by 50,000, 100,000 and 300,000 times and the quantity of dissolving oxygen prior to and after storage at a constant temperature (20° C., for 5 days) was determined and BOD was calculated. Chrome oxide was oxidized by nitric acid or perchloric acid and the optical density at 375 nm was determined.

In group (A), BOD value per 1 kg of feed in the additive group reduced by 56.1 to 59.8% compared with that in the control group. From these results, it is proved that the additive of the present invention promotes digestion and absorption of feeds, reduces the pollution of water for cultivation derived from the feces excreted from fish, and offers better circumstances for cultivating healthy fish.

Example 3

Composition of the feed additive per 1000 g:

| | |
|---|---|
| Active principle of LB (Note 1) ($7 \times 10^8$ bacteria/g) | 10 g |
| Active principle of SB (spore) (Note 2) ($5 \times 10^8$/g) | 50 g |
| Active principle of BB (spore) (Note 3) ($8 \times 10^7$/g) | 75 g |
| Proteinase (Note 4) | 130,000 units |
| Lipase (Note 5) | 350,000 units |
| Yeast (a nutrition supplement) | proper quantity |
| Corn starch (a nutrition supplement and vehicle) | proper quantity |
| Calcium carbonate (a vehicle) | proper quantity |

(Note 1) *Bifidobacterium bifidum* was used.
(Note 2) *Bacillus mesentericus* was used.
(Note 3) *Clostridium butyricum* was used.
(Note 4) An alkaline proteinase yielded from the bacteria belonging to Genus Aspergillus.
(Note 5) An alkaline lipase yielded from the bacteria belonging to Genus Rhizopus.

Examples of Use of Additive of the Invention

The effect of the feed additive of the present invention on the growth of eel

The eel, *Anguilla japonica*, were divided for study into 2 groups, a young eel group (67-83 g). The water tank for the young eel group was 6 m × 6 m × 1 m (depth) in size and 10 m × 10 m × 1 m (depth) for the adult eel group, and an additive addition group and additive free group (control group) were made in each group. Spring water, 25° C. to 33° C., was supplied at a water exchange rate of 4.5 to 6.0%.

The assorted feed consisting of animal feed 67%, wheat 23%, plant oil grounds 3%, and others 7% was used as a basic feed, to which the additive of the present invention was added in an amount of 2.5%. The quantity of feed supplied was equal to 1.0-3.5% of the body weight and adjusted after observing the degree of ingestion. The culturing period was 35 days in the young eel group and 80 days in the adult eel group.

In both groups, the of the body weight and the feed efficiency were improved by adding the additive. This finding proved that the additive had a good effect on digestion and absorption of feeds. The number of dead eel was also observed to be statistically significant.

| Test Result of Eel Cultivation | | | | |
|---|---|---|---|---|
| | Young Eel | | Adult Eel | |
| | Addition | Control | Addition | Control |
| Total Weight (kg) at the Beginning | 540 | 570 | 1,700 | 1,750 |
| Number of Fish at the Beginning | 54,000 | 57,000 | 20,400 | 26,250 |
| Average Body Weight (g) at the Beginning | 10 | 10 | 83 | 67 |
| Number of the Dead | 9 | 25 | 5 | 17 |
| Total Weight (kg) at the End | 1,172 | 1,117 | 2,447 | 2,275 |
| Number of Fish at the End | 53,991 | 56,975 | 20,395 | 26,233 |
| Average Body Weight (g) at the End | 21.7 | 19.6 | 120 | 87 |
| Quantity of Feed (kg) | 763 | 779 | 624 | 826 |
| Increase Rate of Body Weight (%) | 217 | 196 | 144 | 130 |
| Feed Efficiency (%) | 76.5 | 71.7 | 95.9 | 84.1 |

What is claimed is:

1. A feed additive for fish cultivation which contains a combination comprising, as active components, a proteinase, a lipase, and a viable mixture of three kinds of bacteria consisting of lactic acid producing bacteria, saccarificating bacteria, and butyric acid producing bacteria, wherein the bacteria are capable of coexisting in a symbiotic relationship and wherein the components of the combination are present in a proportion effective to improve the digestion and absorption by fish of fish feed supplemented therewith.

2. The feed additive for fish cultivation according to claim 1, in which the lactic acid producing bacteria is *Streptococcus faecalis*, saccarificating bacteria *Bacillus mesentericus*, and butyric acid producing bacteria *Clostridium butyricum*.

3. The feed additive for fish cultivation according to claim 1 or claim 2, in which the proteinase is yielded from *Aspergillus melleus* and shows a maximum enzymatic activity at about pH 8.0.

4. The feed additive for fish cultivation according to claim 3 in which yeast is included with said combination as a nutritional supplement in an amount effective to promote the growth of the viable bacteria.

5. The feed additive for fish cultivation according to claim 1, in which yeast is included with said combination as a nutritional supplement in an amount effective to promote the growth of the viable bacteria.

6. The feed additive for fish cultivation according to claim 1, in which the saccarificating bacteria are effective to increase the concentration of the lactic acid producing bacteria, and the lactic acid producing bacteria and the butyric acid bacteria are effective to increase the concentration of each other.

7. The feed additive for fish cultivation according to claim 1, in which the viable mixture of three kinds of bacteria consists of about 1 to 8 parts by weight of lactic acid producing bacteria about 1 to 8 parts by weight of saccarificating bacteria, and about 1 part by weight of butyric acid producing bacteria.

8. The feed additive for fish cultivation according to claim 1, in which the proteinase is a bacterial proteinase selected from actinomyces proteinase and filamentous fungus proteinase and the lipase is obtained from bacteria selected from bacteria belonging to the Genus Rhizopus and Candida.

9. In a feed for fish, the improvement comprising the feed supplemented with an additive in an amount effective to improve the utilization by fish of the fish feed, wherein the additive is composed of a combination comprising, as active components, a proteinase, a lipase, and a viable mixture of three kinds of bacteria consisting of lactic acid producing bacteria, saccarificating bacteria, and butyric acid producing bacteria, wherein the bacteria are capable of coexisting in a symbiotic relationship and wherein the components of the combination are present in a proportion effective to improve the digestion and absorption by fish of the fish feed.

10. The fish feed according to claim 9, in which yeast is included with said combination as a nutritional supplement in an amount effective to promote the growth of the viable bacteria.

11. The fish feed according to claim 9, in which lactic acid producing bacteria is *Streptococcus faecalis*, the saccarificating bacteria is *Bacillus mesentericus*, and the butyric acid producing bacteria is *Clostridium butyricum*.

12. The fish feed according to claim 9, in which the viable mixture of three kinds of bacteria consists of about 1 to 8 parts by weight of lactic acid producing bacteria, about 1 to 8 parts by weight of saccarificating bacteria, and about 1 part by weight of butyric acid producing bacteria.

13. The fish feed according to claim 9, in which the proteinase is a bacterial proteinase selected from actinomyces proteinase and filamentous fungus proteinase and the lipase is obtained from bacteria selected from bacteria belonging to the Genus Rhizopus and Candida.

14. The fish feed according to claim 9, in which additive is present in the feed in an amount of about 0.5–2.5% by weight.

15. A method of improving fish feed which comprises adding to said feed the composition defined in claim 1 in an amount effective to improve the digestion and absorption by fish of the fish feed.

16. A method of improving fish feed which comprises adding to said feed the composition defined in claim 5 in an amount effective to improve the digestion and absorption by fish of the fish feed.

17. A method of improving fish feed according to claim 15, wherein the additive is added to the fish feed in an amount of about 0.5–2.5% by weight.

18. A method of cutivating fish comprising feeding said fish the feed defined in claim 9 in an amount effective to cause the fish to grow to the desired size.

19. A method of cutivating fish comprising feeding said fish the feed defined in claim 10 in an amount effective to cause the fish to grow to the desired size.

20. A method of cutivating fish comprising feeding said fish the feed defined in claim 14 in an amount effective to cause the fish to grow to the desired size.

* * * * *